United States Patent [19]

Blackstone

[11] 4,401,111
[45] Aug. 30, 1983

[54] CERVICAL SPINE COLLAR

[76] Inventor: Ralf W. Blackstone, 4678 Barker Way, Long Beach, Calif. 90814

[21] Appl. No.: 201,425

[22] Filed: Oct. 28, 1980

[51] Int. Cl.³ .............................................. A61H 1/02
[52] U.S. Cl. .............................. 128/75; 128/DIG. 23
[58] Field of Search .................. 128/75, 76, 87 B, 68, 128/80, DIG. 23; 272/94

[56] References Cited

U.S. PATENT DOCUMENTS

| | | | |
|---|---|---|---|
| 3,285,243 | 11/1966 | Yellin | 128/75 |
| 3,343,532 | 9/1967 | Zumaglini | 128/75 |
| 4,043,325 | 8/1977 | Ochs | 128/75 |
| 4,161,946 | 7/1979 | Zuesse | 128/75 |

Primary Examiner—Richard C. Pinkham
Assistant Examiner—T. Brown
Attorney, Agent, or Firm—Gunn, Lee & Jackson

[57] ABSTRACT

A cervical spine collar comprising a superstructure and a distracting cuff. The superstructure is molded into a configuration having occipital buttresses and mandible contours on a superior surface while an inferior surface has a longitudinal extending slot. The slot receives an upper portion of a fin having attached to a lower portion an inflatable balloon, the fin and balloon comprising a detachable distracting cuff. The distracting cuff may also be permanently attached to the inferior surface of the superstructure. When the distracting cuff is in position relative to the superstructure and the invention collar is secured to a victim having possible cervical spine injury, the inflatable balloon is inflated thereby forcing the head and neck of the victim into a posture that relieves pressure on the cervical spine area and prohibits possible damaging extension/flexion movement by the victim.

5 Claims, 5 Drawing Figures

CERVICAL SPINE COLLAR

BACKGROUND OF THE INVENTION

In accidents involving possible injury or fractures to the cervical spine, it is important to stabilize the cervical spine as soon as possible. Movement of victims with cervical spine injuries often causes additional cervical injury, spinal cord trauma, and paralysis. Flexive movement of the cervical spine are especially dangerous as 80-90% of spinal cord injuries occuring after the initial cervical spine injury are associated with this movement. The cervical spine collar of the present invention provides emergency stabilization of the cervical spine of a victim at the scene of an accident or trauma prior to moving the victim. The invention cervical spine collar positions the cervical spine in approximately 15 degrees of extension with a distracting force equal to the weight of the head or any portion thereof. In this position, pressure is taken off the fractured cervical vertebrae and the head is arrested from movements which might drive fractured cervical vertebra bone fragments into the spinal cord.

The invention cervical spine collar has two major component parts, a superstructure and a distracting cuff, both of which are longitudinally flexible. This facilitates placing the cervical spine collar about the injured person's neck without moving the neck. Thereafter an inflatable portion of the distracting cuff is inflated to distract and arrest the injured person's neck.

BRIEF DESCRIPTION OF THE PRIOR ART

Several cervical collars utilized in instances of possible cervical spinal injuries are known in the prior art. A cervical collar described in U.S. Pat. No. 3,285,244 to G. W. Cottrell comprises an adjustable member that encircles the neck of the wearer with a second member pivotally secured to the adjustable neck piece, the upper and lower edges of the cervical collar having inflatable pneumatic casings, the inflatable casings providing a means to apply variable traction on the cervical spine in accordance to the degree inflation of the casing. The Cottrell collar is not adapted for emergency use, does not properly support the head in the proper angle for maximum safety and realignment of slightly displaced vertebrae or fragments and is further not adaptable for application upon a patient at a predetermined distracting force upon the cervical spine.

U.S. Pat. No. 3,164,151 to E. D. Vere Nicoll, an inflatable splint to be used as an inflatable surgical collar or neck brace, comprises a plurality of vertically oriented tubular columns of air in communication with each other than when inflated around the neck of an injured person provide adequate support to an injured neck and head of the victim. A depression that receives the chin of the wearer in the inflatable splint tends to prevent and restrain rotational movement of the head of the victim. The Nicoll collar is extremely limited in its vertical adaptability and may only be used upon a single body size and type if the proper distraction force and angle of extension are to be obtained. Since an ambulance would not only have to maintain many such Nicoll collars, but the attendants would also have to instantly select the correct size collar upon pain of causing further spinal injury, the Nicoll collar is inadequate for use as an emergency cervical spine stabilization device.

The inflatable cervical collar disclosed in U.S. Pat. No. 3,765,412 to Ayub K. Ommaya, et al, is adapted to be worn by occupant of a motor vehicle. The cervical collar has a source of compressed gas connected to it, as well as triggering means associated with the compressed gas source. When the collar is inflated, such as in the case of a rear end collision, rotation of the head of the wearer of the collar is reduced or prohibited thus preventing a whiplash-like head or neck injury. Failure to provide the steadying support of a vertically inflexible superstructure as is shown in the invention cervical spine collar prevents stabilization of the neck in the secure manner or in the proper angle of extension as is required for proper emergency care. The cervical collar of the Ommaya, et al patent is therefore a preventive device unsuited to emergency use after cervical spine injury as in the case of the invention cervical spine collar.

Another inflatable cervical collar is disclosed in U.S. Pat. No. 3,343,532 to G. Zumaglini. The Zumaglini collar comprises a semi-rigid case of synthetic resin having a bottom portion adapted to bear on the clavicular region of a victim, a middle portion encircling the neck of a victim, and a top portion provided with rests for the sub-mandibular and occipital regions. In order to fit the cervical collar on a victim, the semi-rigid cast is slotted on one side, the facing edges of the slot being provided with a closure, such as a sliding clasp fastener. The Zumaglini cervical collar is used as an alternative to the Styker frame bed and Crutchfield tongs in long-term treatment where full immobilization of the cervical rachis, traction and extension of a permanent character are desired.

It further has such a high profile as to make it extremely dangerous to an unconscious cervically injured victim due to the displacement of the neck necessary to secure the collar. Additionally the Zumaglini collar is inappropriate for use in emergency situations because the side attachement upon which the collar relies prevents the crucial lateral cervical spine X ray from being taken while the neck is secured within the collar.

SUMMARY OF THE INVENTION

It is an object of the present invention to provide a cervical spine collar to be utilized in emergency stabilization of the traumatized cervical spine. The cervical spine collar comprises a superstructure and an inflatable distracting cuff engaging the lower portion of the superstructure. The cervical spine collar when in position on an injured person holds the injured person's head in approximately 15 degree extension and distracts the head at a predetermined proper force to relieve pressure on the spine, prevent further injury to the cervical spine and use the paraspinous muscles and ligaments to realign any displaced vertebrae or fragments thus relieving pressure from the spinal cord.

DESCRIPTION OF THE PREFERRED EMBODIMENT

Figure 1:
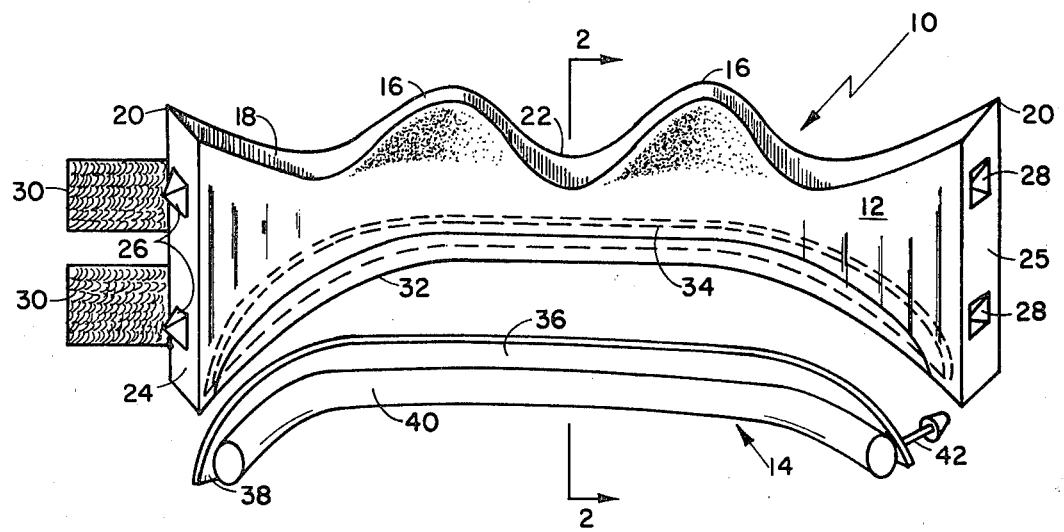
FIG. 1 is an exploded view of the invention cervical spine collar.

FIG. 1 shows the invention cervical spine collar 10 comprising two main component parts, superstructure 12 and inflatable distracting cuff 14. The two component parts will be discussed first and subsequently a method of using the collar will be discussed.

Superstructure 12 of the invention cervical spine collar 10 is composed entirely of a single material and is constructed to be fit around the neck of an accident victim. The superstructure must be longitudinally flexible for wrapping around the neck of the victim while allowing essentially no flexing in the latitudinally direction of the superstructure to prevent flexion/extension movement of the neck. The selected material must therefore be both rigid enough to hold an accident victim's head in a fixed position and flexible enough to allow a paramedic or an ambulance attendant to insert the invention cervical spine collar without moving the victim. A preferred material is a molded, high density rubber, such as 30-shore Neoprene artificial rubber with a maximum thickness of 1 inch.

Alternatively, the superstructure 12 may be comprised of a thinner and/or more flexible material but be supported by a plurality of stablizing ribs. A hollow form of the superstructure 12 having eight ribs molded in a single piece form a malleable plastic may thus be used to produce a superstructure 12 at a lower cost without sacrificing the rigidity needed to sufficiently immobilize the victim's head. The flexible material would comprise a hollow superstructure form which would abut against the victim's head and neck and the strong rigid ribs inserted within the hollow space to additionally support the superstructure 12. The ribs would each extend latitudinally within the superstructure and be longitudinally spaced approximately equadistantly from each other to provide a superstructure sufficiently strong and rigid laterally to immobilize the victim's head once attached but still be sufficiently longitudinally flexible to allow easy application of the collar 10 about the victim's neck.

The superior surface of the superstructure 12 is molded to have both occipital buttresses 16 and mandible contours 18. The superior surface is of a configuration to attest the head of a victim to be held in a 15 degree extension. The occipital buttresses 16 conform to each occipital tuberosity of the skull an the anterior superior surface (mandible contours 18) follow the contours of the mandible.

Mandible contours 18 terminate at the forward edge 20 of the superstructure 10, the forward edges 20 meeting when the collar 10 is in place at the area approximately under the chin of the victim. A valley 22 located between the occipital buttresses 16 cradles the rear portion of the head of the victim. Th angle of the mandible contours 18 in relation to the rest of the superstructure 10 is such that when the invention cervial spine collar 10 is in position on the victim, the head of the victim is held in a 15 degree extension and is prevented from flexing in a forward downward motion.

Figure 4:
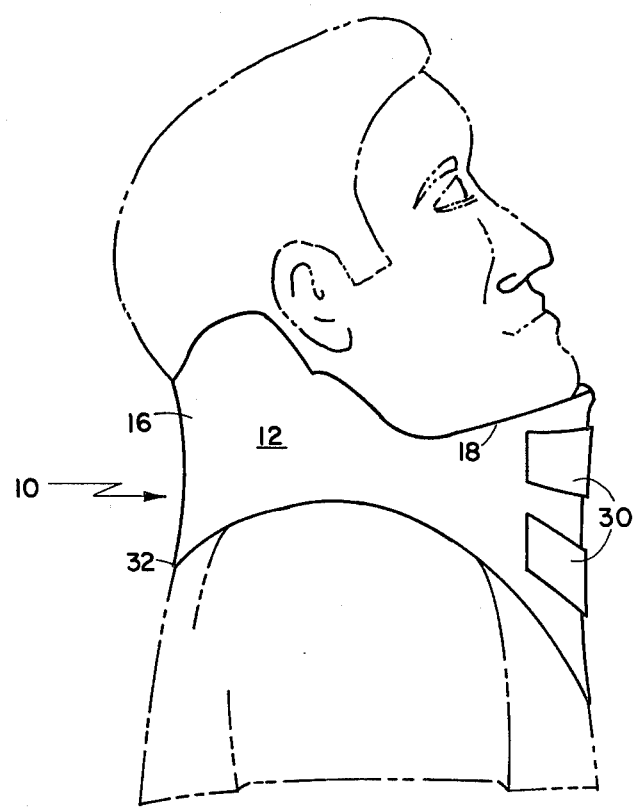
FIG. 4 is a slide pictorial representation of an accident victim wearing the invention cervical spine collar.

As shown in FIG. 1 and in detail in FIG. 4, on one end 24 of the superstructure 10 are pyramidal protrusions 26 that cooperate with pyramidal recesses 28 on a second end 25 to hold cervical spine collar 10 in proper alignment. Securing straps 30 attached to superstructure 12 on the same side as pyramidal protrusions 26 hold pyramidal protrusions 26 and pyramidal recesses 24 in position by attaching to securing grips (not shown) located on the same side of the superstructure 12 as pyramidal recesses 24. Thus the securing straps 30 function to secure the ends of the superstructure 24 and 25 laterally together and enable pyramidal protrusions 26 and recesses 28 to secure the superstructure 12 vertically. The combination permits rapid placement and securing of the collar 10 about the victim in a manner which effectively welds the superstructure 12 into a single solid unit. The securing straps 30 and grips are preferably made of a Velcro-type material to provide both quick attachability and releaseability together with a secure joinder.

As can be more easily seen in FIGS. 4 and 5, the inferior surface of superstructure 12 is contoured to follow the shape of the victim's shoulders and chest, the inferior edge 32 extending slightly below the level of the shoulders in the rear, following the shape of the shoulders, and then extending down the anterior chest to the Angle of Lewis 42 (manubiosternal junction). This configuration is needed to properly arrest the cervical spine from damaging extension or flexion movement of the neck. None of the cervical spine collars found in the prior art are adequate to properly secure the neck for the reason, among others, that the inferior surfaces of the prior art collars do not extend either a sufficient distance below the level of the shoulders in the rear to prevent neck extension or to the manubiosternal junction to prevent neck flexion. The invention cervical spine collar is thus uniquely adapted for aiding victims of cervical spine trauma in emergency situations. Without such extraordinary measures being taken to totally arrest the head, moving the body of the victim from the accident site to a hospital often causes serious further cervical spine injury.

Superiorly directed in the interior region of the superstructure 12 is slot 34 preferably 1" in depth. Slot 34 extends approximately the entire longitudinal length of the superstructure 12 and retains fin 36 of inflatable distracting cuff 14.

Distracting cuff 14 provides optimum fitting of a fairly universal sized collar to each particular accident victim. Distracting cuff 14 when in position in slot 34 of superstructure 12 provides a distracting force up to equal the weight of the victim's head distracting force of this measure utilizes the paraspinous muscles and ligaments to realign any slightly displaced vertebrae and/or fragments and thus relieves pressure from off the spinal cord. Ditracting cuff 14 is composed of four parts, fin 36, guard plate 38, inflatable balloon 40 and valve stem 42. Fin 36 fits into slot 34 of superstructure 12 and holds distracting cuff 14 in position relative to superstructure 12. Fin 36 is preferably composed of hard polyethylene plastic although many other rigid supporting materials may be utilized. Guard plate 38 is fused or molded to the lower portion of fin 36 and provides the attachment means for inflatable balloon 40. Guard plate 38 is preferably made from a polyethylene material which is softer than that used for fin 36.

The primary purpose of designing the collar 10 to having a distracting cuff 14 which is detachable is to account for the anticipated shorter usable life of the distracting cuff 14 than the superstructure 12. Upon the distracting cuff 14 being judged untrustworthy, it may easily be discarded and another substituted in its place. Furthermore, it is possible to further extend the universality of a single superstructure 12 by having more than one size distracting cuff 14 available to be fit upon the superstructure 10 upon observing the size of the victim.

Although shown in FIGS. 1-4 as having a superstructure 12 and a detachable distracting cuff 14, the invention cervical spine collar also contemplates an inflatable distractive cuff permanently secured to superstructure 12. Fin 36 is omitted and balloon 40 is glued directly to superstructure 12, thereby permanently securing distracting cuff 14 in place. In such cases when superstructure 12 and distracting cuff 14 are an integral unit, the entire cervical spine collar is disposable in contrast to the collar described above and depicted in FIGS. 1-4. Whether the invention cervical spine collar is two separate components, superstructure and detachable distracting cuff, or an integral unit, the invention collar will function in the same manner and provide the same advantages in both embodiments.

With the head distracted at the proper angle of extension and with the proper amount of force, the paraspinous muscles and ligaments of the victim relign any slightly displaced vertebrae or fragments and pressure on the spinal cord is relieved. Inflatable balloon 40 is preferably a cylindrical plastic balloon made from material similar to that used on the inflatable cuff of present day endotracheal tubes. Valve stem 42 is also similar to types used on present day endotracheal tubes and is preferably attached to balloon 40 at an easily accessible location. Because the paraspinous muscles and ligaments of the victim are properly aligned about the spinal cord when the head is held at a 15 degree extension angle with a force equal to the weight of the victim's head, the attendants will estimate the weight of the victim's head by roughly judging its size and will inflate the inflatable balloon with an air pressure equivalent to that weight. Thus inflating balloon 40 to preferably approximately 10-15 pounds of pressure via valve stem 42 in accordance with the size of the victim's head exerted on his spine. Furthermore, with fin 36 of distracting cuff 14 properly positioned in slot 34 of superstructure 12 and balloon 40 inflated a correct amount, a victim's head is completely immobilized thus preventing further or increased injury to the cervical area of the body.

Figure 2:
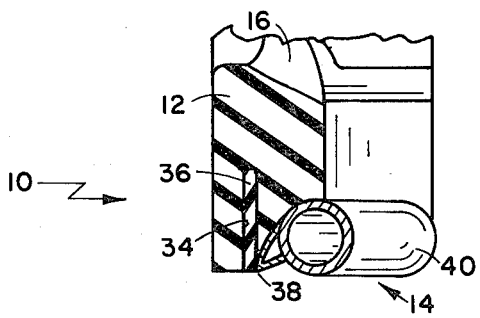
FIG. 2 is a cross-sectional view of the invention cervical spine collar taken along line 2—2 of FIG. 1.
Figure 3:
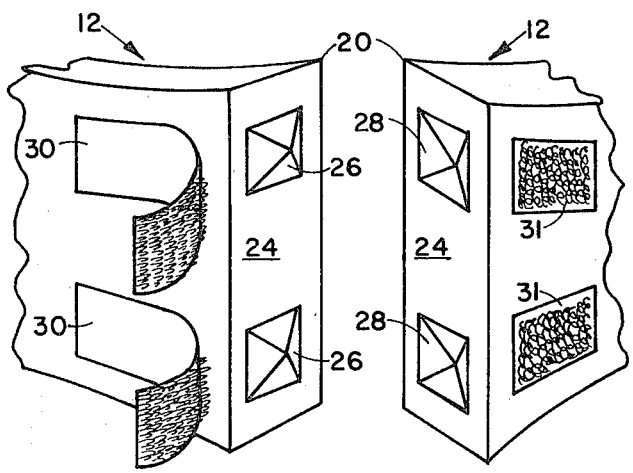
FIG. 3 is a perspective view of the ends of the invention cervical spine collar illustrating the fastening means.

The relationship of the distracting cuff 14 to the superstructure 12 is shown in FIG. 2. This end view of the invention cervical spine collar 10 shows fin 36 of distracting cuff 14 fitting in slot 34 in superstructure 12. Attached to the inferior portion of fin 36 is guard plate 38. Secured to guard plate 38 is inflatable balloon 40. As can be seen from FIG. 2, inflating balloon 40 forces fin 36 up into slot 34 of superstructure 12.

Figure 5:
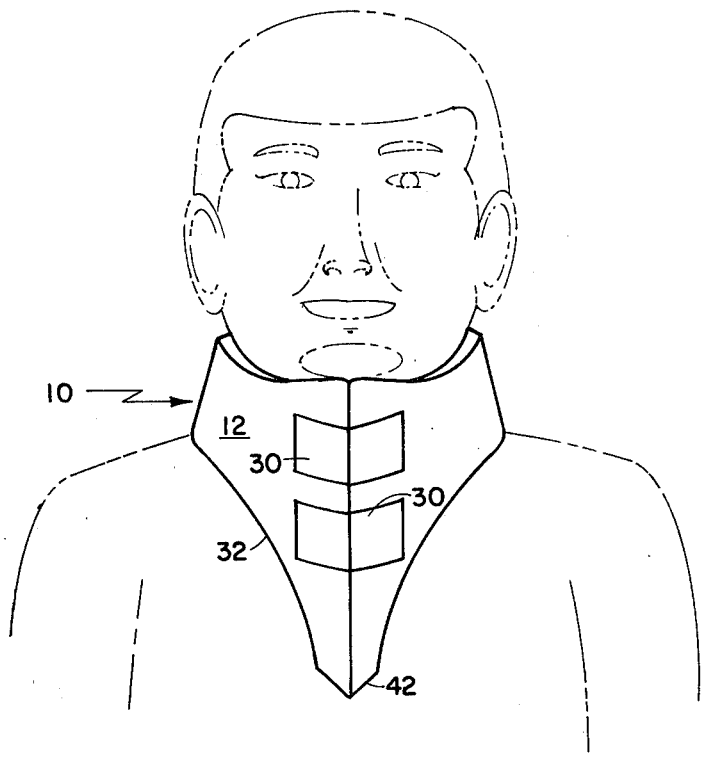
FIG. 5 is a frontal pictorial representation of an accident victim wearing the invention cervical spine collar.

The invention cervical spine collar 10 when in position on an accident victim is shown in FIGS. 4 and 5. Occipital buttress 16 holds the occipital tuberosity of the skull and provides firm support to the skull. It limits backward motion (extension) of the neck and aids in immobilizing and distracting the head and the neck of the accident victim. The anterior of the invention cervical spine collar 10, the mandible contour 18, is designed and constructed to lift the chin of the accident victim upward to a 15 degree angle of extension. The inferior edge 32 of the cervical spine collar 10 conforms to the shoulders of the victim and extends downward on the chest of the victim to the Angle of Lewis 42. Securing straps 30 affixed to the outer surface of the collar 10, secure the collar 10 in place once the edges 20 have been aligned by means of pyramidal protrusions 26 and pyramidal recesses 28.

Thus when in position, (superstructure 12 engaging the victim's head, distracting cuff 14 contacting the shoulders and chest of the victim, and inflatable balloon 40 inflated), the invention cervical spine collar immobilizes the cervical spine, places the head of the victim in a 15 degree angle of extension and uses a distraction force equal to the weight of the head to relive any harmful pressures from fractured cervical vertebrae.

In operation the cervical spine collar 10, already having the distracting cuff 14 in position, is slipped under the neck of an accident victim without unnecessarily moving the victim and fastened securely about the victim's neck by means of pyramidal protrusions 26 and recesses 28 and straps 30 and grips 31. After securing the collar 10 in position, balloon 40 is inflated by means of valve stem 42 to approximately 10-15 pounds of pressure depending upon the victim's body size. The pressure of the inflated collar 10 thus distracts the full weight of the head of the victim and allows the paraspinous muscles and ligaments to realign any slightly displaced vertebrae or fragments and helps relieve the pressure on the spinal cord of the victim. The invention cervical spine collar 10 thus provides emergency relief of the cervical spine in trauma victims with possible fractures.

The collar also provides emergency stabilization to prevent damaging flexive movement by a chin-to-sternum reinforced front edge so that even an uncooperative and combative trauma victim cannot flex his neck. The highly buttressed superstructure of the invention cervical collar about the occipital tubercles prevents the hyperextension of the neck of the victim. Locating the invention cervical spine collar opening and closing positions (ends 24 and 25 of the collar 10) anteriorly enables an emergency room physician to easily remove the collar and reattach the collar as may be necessary for access to the esophagus for a tracheotomy or other respiratory relief procedure. Further, the facility of rapid removal aids in providing easy accessibility to the victim for neck X rays which are often the first diagnostic test performed in evaluating a damaged neck for fractures.

The invention cervical spine collar 10 is intended for short term immobilization of possible cervical spine fractures until X rays rule out or confirm fracture of the spine and Crutchfield tongs and Stryker-frame bed or Halo apparatus may be deemed necessary. The features of total immobilization with sufficient anterior and posterior support to withstand great force to the head, proper angular extension of the head and properly balancing of the weight of the head to cause alleviation of pressure on the spinal cord, ease of applying the collar without further injuring the victim, location of the closure mechanism out of the path of lateral diagnostic neck X rays and anterior location of a neck access for access to the victim's respiratory tract are each novel to the invention cervical spine collar.

It is apparent from the above description that significant improvements in the art of emergency care of victims of cervical spine trauma are achieved by the instant invention.

While the invention has been described in connection with the preferred embodiment, it is not intended to limit the invention to the particular forms set forth, but, on the contrary, it is intended to cover such alternatives, modifications and equivalents as may be included within the spirit and scope of the invention as defined by the appended claims.

I claim:

1. A cervical spine collar providing head and neck stabilization relative to the upper spine of a victim having possible cervical spine injury comprising;
   (a) an elongated superstructure, said superstructure being substantially planar, longitudinally flexible, latitudinally rigid and adapted to be closely positioned about a human neck;
   (b) a fastening means located upon the longitudinal ends of said superstructure for fastening said longitudinal ends to each other, said fastening means and said superstructure adapted to facilitate location of said fastening means at the anterior face of said neck when said collar is positioned about said neck; wherein said fastening means comprises: pyramidal protrusions and securing straps located on a first end of said superstructure; and pyramidal recesses and securing grips located on a second end of said superstructure, said protrusions and said recess cooperating to hold said collar in proper lateral alignment while said securing straps cooperate with said securing grips to secure said collar longitudinally about on said neck of said victim;
   (c) a superior surface of said superstructure contoured to closely fit about the lower portion of a human head to prevent movement of said head; and
   (d) an inferior surface of said superstructure contoured to closely fit about the shoulder area of a human upper torso to prevent substantial movement of said superstructure.

2. The collar of claim 1 further comprising a distracting cuff designed and constructed to retain air at a substantially constant pressure for at least one hour and additionally comprises an air valve for controlling inflation and deflation of said distracting cuff to permit selection and maintenance of a desired distraction force by said collar upon said head and a fin adapted to fit within a slot within said inferior surface of said superstructure.

3. A cervical spine collar providing head and neck stabilization relative to the upper spine of a victim having possible cervical spine injury comprising;
   (a) an elongated superstructure, said superstructure being substantially planar, longitudinally flexible, latitudinally rigid and adapted to be closely positioned about a human neck;
   (b) a fastening means located upon the longitudinal ends of said superstructure for fastening said longitudinal ends to each other, said fastening means and said superstructure adapted to facilitate location of said fastening means at the anterior face of said neck when said collar is positioned about said neck;
   (c) a superior surface of said superstructure contoured to closely fit about the lower portion of a human head to prevent movement of said head;
   (d) an inferior surface of said superstructure contoured to closely fit about the shoulder area of a human upper torso to prevent substantial movement of said superstructure;
   (e) a distracting cuff fixed upon said inferior surface to rest upon said shoulder area and said upper chest area, said distracting cuff being inflatable to separate said superstructure from said shoulder area and said upper chest area and distract said head from said shoulder area and said upper chest area for immobilizing said head and said neck relative to said shoulder and said upper chest areas; and
   (f) said superstructure additionally comprising at least one longitudinal slot upon the lower edge of said inferior surface and said distracting cuff additionally comprising at least one longitudinal fin upon the upper surface of said distracting cuff, said slot and said fin adapted to permit said fin to be fixed within said slot to secure said distractable cuff to said inferior surface, said slot and said fin further adapted to permit said fin to be removed from said slot to remove said distracting cuff from said inferior surface and said slot further adapted to permit insertion of a second fin within said slot to fix a second distracting cuff to said inferior surface.

4. The collar of claim 3 wherein said distracting cuff is designed and constructed to retain air at a substantially constant pressure for at least one hour and additionally comprises an air valve for controlling inflation and deflation of said distracting cuff to permit selection and maintenance of a desired distraction force by said collar upon said head.

5. A cervical spine collar providing head and neck stabilization relative to the upper spine of a victim having possible cervical spine injury comprising;
   (a) an elongated superstructure comprised of a single unit, said superstructure being substantially planar, longitudinally flexible, latitudinally rigid and adapted to be closely positioned about a human neck;
   (b) a fastening means located upon the longitudinal ends of said superstructure for fastening said longitudinal ends to each other, said fastening means and said superstructure adapted to facilitate location of said fastening means at the anterior face of said neck when said collar is positioned about said neck;
   (c) the posterior portion of said inferior surface extending at least down to the level of said shoulders for preventing extension of said neck and said anterior portion of said inferior surface extending at least down to the level of the victim's manubiosternal junction for preventing flexion of said neck;
   (d) the posterior portion of said superior surface extending upward to form occipital buttresses contoured to closely fit about the occipital tuberosities of said victim's head and said anterior portion of said superior surface is contoured to closely fit about the mandible of said victim's head, said contouring of said superior surface preventing substantial flexion or extension of said neck when said superior surface is clearly positioned about said lower portion of said human head; and
   (e) a distracting cuff fixed upon said inferior surface to rest upon said shoulder area and said upper chest area, said distracting cuff being inflatable to separate said superstructure from said shoulder area and said upper chest area and distract said head from said shoulder area and said upper chest area for immobilizing said head and said neck relative to said shoulder and said upper chest areas and wherein said distracting cuff is designed and constructed to retain air at a substantially constant pressure for at least one hour and additionally comprises an air valve for controlling inflation and deflation of said distracting cuff to permit selection and maintenance of a desired distraction force by said collar upon said head, and a fine adapted to fit within a slot within said inferior surface with said superstructure for detachably attaching said distracting cuff.

* * * * *